United States Patent [19]

Perrotti et al.

[11] 4,042,609
[45] Aug. 16, 1977

[54] σ AND π ORGANIC COMPLEXES OF TRANSITION METALS AND PROCESS FOR THE PREPARATION THEREOF

[75] Inventors: Emilio Perrotti; Mario Clerici, both of San Donato Milanese, Italy

[73] Assignee: Snam Progetti S.p.A., Milan, Italy

[21] Appl. No.: 654,350

[22] Filed: Feb. 2, 1976

Related U.S. Application Data

[63] Continuation of Ser. No. 419,374, Nov. 27, 1973, abandoned.

[30] Foreign Application Priority Data

Nov. 29, 1972  Italy .................................. 32211/72

[51] Int. Cl.² .......................... C07F 15/00; C07F 13/00
[52] U.S. Cl. ............................. 260/429 R; 252/431 P; 260/642 E
[58] Field of Search ................. 260/429 R; 252/431 P

[56] References Cited

U.S. PATENT DOCUMENTS

| | | | |
|---|---|---|---|
| 3,468,921 | 9/1969 | Wilke | 260/429 R |
| 3,527,818 | 9/1970 | Mason et al. | 260/429 R |
| 3,622,607 | 11/1971 | Fenton | 260/429 R |
| 3,720,697 | 3/1973 | Fenton | 260/429 R |

OTHER PUBLICATIONS

Coates et al., Principles of Organometallic Chemistry, Methuon & Co., London, 1970, pp. 150-157.
Schunn, Inorg. Chem. 9(1970), pp. 2567-2572.
Perego et al., J. Orgmet. Chem. 54(1973), pp. C51-C52.
Takesada et al., Chem. Abst. 70(1969), No. 87940y.

Primary Examiner—Arthur P. Demers
Attorney, Agent, or Firm—Ralph M. Watson

[57] ABSTRACT

A compound having catalytic properties which is a σ or π organic complex of a transition metal represented by the general formula: $M(A)_n (L-C) (L)_m$, wherein M is Ir or Re; L is a member of the group consisting of alkyl and aryl phosphines; (L-C) is (a) an alkyl or aryl phosphine ligand wherein a C-H bond is reacted with the central M atom to which the ligand is coordinated, and a metal-carbon bond is formed, or (b) a π-allyl radical; A is a linear monoolefin having from 2 to 5 carbon atoms or a cyclic monoolefin having from 6 to 8 carbon atoms; n is a number in the range of 0 to 2 and is always zero when L-C is a π-allyl radical; and m is a number from 1 to 3 which satisfies the valence of M, is prepared by reacting a hydride complex represented by the general formula: $MHL_{n_1}$ wherein M and L have the meaning given above, x is in the range from 5 to 7 and $n_1$ is a number from 2 to 3 which satisfies the valence of M, with a linear monoolefin having from 2 to 5 carbon atoms or a cyclic monoolefin having from 6 to 8 carbon atoms.

22 Claims, No Drawings

σ AND π ORGANIC COMPLEXES OF TRANSITION METALS AND PROCESS FOR THE PREPARATION THEREOF

This is an continuation, of application Ser. No. 419,374 filed Nov. 27, 1973 and now abandoned.

The present invention relates to novel σ and π organic complexes of transition metals and to the process for the preparation thereof. It is known that the metalorganic complexes of the transition metals may be employed as catalysts in many reactions such as hydrogenations, carbonylations and oxidations.

It is also known that, in order to carry out a definite reaction, the catalytic species responsible therefor can be formed provided that the starting complex has suitable characteristics as to the metal type and the oxidation state thereof, and that the ligands and the reaction conditions are appropriate.

We have found that it is possible to synthesize transition metal metalorganic complexes, wherein the metal is in a low oxidation state and at the same time contains a small number of strong ligands, these characteristics being very good with respect to the ensuing uses of the complexes that we shall refer to hereinafter.

The metalorganic complexes, which are the subject of the present invention, have the following general formula $$M(A)_n (L-C) (L)_m$$

in which M is the transition metal preferably selected from Mo, W, Ti, Os, Ir, Re, Rh and Ru; L is selected from phosphines, arsines and stibines (both the alkyl and aryl ones); (L-C) is selected from (a) phosphines, arsines and stibines (alkyl or aryl) in which a C-H bond reacted with the central M atom to which the ligand is coordinated to form a metal-carbonium bond or (b) a π-allyl radical; A is an olefin; n is in the range from 0 to 2 and m from 1 to 3 according to the metal; in the case of diolefins $n=1$; n is always zero when (L-C) is a π-allyl radical.

The aforesaid complexes are obtained by a process, which is therefore a second aspect of the present invention, based on a reaction between hydride complexes of the proposed metal and olefins, in inert solvents or in the same olefin acting as a solvent.

The starting products, which surprisingly proved very suitable for the reactions giving high yields, are hydride complexes, which have no different anionic ligand, corresponding to the general formula $MH_xLn_1$ wherein x is in the range from 5 to 7, L is a ligand selected from the aforesaid ones, and $n_1$ is 2 or 3 according to the metal. The preparation of such hydrides is disclosed in: Journal of Chemical Society, 1965 (6974); Journal of American Chemical Society, 92, 1970 (5234); and Chemical Communications, 1970 (703).

The nature of the starting olefine remarkably affects the structure of the final product. Starting from ethylene, compounds are obtained wherein the important feature is the ligand metallation and $n \neq 0$, while higher olefins, as starting material, give rise to complexes wherein $n = 0$ and therefore contain a π-allyl radical.

The process for the preparation of the inventive metalorganic complexes occurs through a reduction of higher hydrides of metal complexes having the aforesaid formula with an olefin, the reaction being carried out either in an inert solvent selected from aromatic or aliphatic hydrocarbons or in absence of any solvent, the same olefin itself acting as a solvent. It is preferable to work in diluted solutions in the presence of solvents wherein the starting product is somewhat soluble so that the transformation thereof occurs at a controlled rate.

It is obvious that any olefin may be employed as a starting material, but use is preferably made of those having a low carbon atom number when crystalline and pure compounds are wished for the following catalytic reactions: therefore use is made of $C_2 - C_5$ olefins, or the $C_6 : - C_8$ cyclic olefins.

The reaction is carried out at a temperature in the range between 0° C and 70° C and at pressures varying from one to 15 atmospheres. Moisture and oxygen must be avoided with great care because of the high reactivity of the complexes.

It is also possible to prepare the complexes wherein $n = 0$, i.e., containing the π-allyl radical (L-C), starting from the complexes having $n = 0$ which are reacted with higher olefins.

The metalorganic complexes which are the subject of the present invention, have a high reactivity towards olefins, compounds containing mobile hydrogen and hydrogen itself.

Particularly, subjected to a hydrogenation at a normal pressure, they give rise again to the starting hydride compounds and to the catalytic hydrogenation of olefins, dienes and acetylenes.

Furthermore they may catalyze hydrogen-transfer reactions between mobile hydrogen containing compounds such as alcohols and alkines towards the formation of alkenes according to the subject-matter of, the Italian Patent No. 896,993, and the corresponding U.S. application, Ser. No. 460,222, field Apr. 11, 1974.

They can be also employed as hydrogen transfer catalysts on the olefins in order to obtain conjugated diene compounds having a trans-trans prevailing configuration, according to the reaction described in the Italian Patent No. 908,842, and the corresponding U.S. Pat. No. 3,849,510.

EXAMPLE 1

$1.5 \times 10^{-3}$ mole of $IrH_5 [(C_6H_5)_3P]_2$ was suspended in 150 cc of anhydrous and degassed benzene, in autoclave under ethylene at a pressure of 8 atmospheres. The mixture was stirred by a magnetic stirrer.

The reaction mixture was brought to 45° C for half an hour and then was cooled to 5° C and maintained for 2 hours at such a temperature. It was concentrated to a low volume by evaporating the solvent under an ethylene stream and then the obtained crystals were separated by filtration under argon and dried under vacuum. They were recrystallized from toluene.

The characterization was performed by a spectrophotometer $$[Ir/ethylene_2 \{P(C_6H_5)_3\} \{P (C_6H_5)_2 (C_6H_4)\}]$$

a. IR: 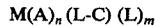 $= 1555$ cm$^-$ b. NMR: $\delta_{CH_2=CH_2} = 2.5$ (at 25° C);

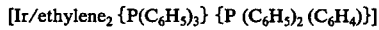

c. Centesimal analysis: agreement with the proposed structures.

d. X rays. By means of this method a very distorted trigonal bipyramidal structure was emphasized around iridium wherein the ligands were: two ethylene molecules, two phosphorous atoms (of phosphines) and a carbon atom (in the ortho-position of a phosphine phenyl) directly bound to iridium: Me-C length = 2.07 A.

EXAMPLE 2

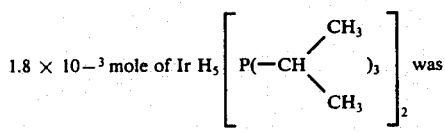

dissolved in 60 cc of anhydrous benzene in autoclave. It was subjected to an ethylene pressure of 10 atmospheres at the temperature of 45° C for about 1 hour, and then it was brought to 0° C for 3 hours. The solvent was removed under a $C_2H_4$ stream at 5° C; the residue was dissolved again by a very small amount of n-pentane (10 cc) and was crystallized at the temperature of −20° C under a $C_2H_4$ atmosphere.

The crystals were separated by filtration under argon and dried under vaccum.

$O_2$ had to be removed with great care during all the reaction and separation steps, owing to the fact that the compound undergoes rapid decomposition in air. This precaution had to be observed also in performing the preceding example.

The characterization was performed through:
a. Centesimal analysis, in agreement with the theoretical one for

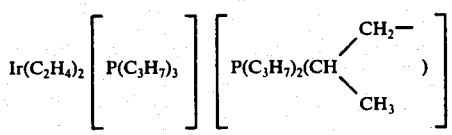

b. NMR δ $CH_2 = CH_2$ from TMS = 2.5 p.p.m. (broad)
c. IR ν $CH_{2=}$ $CH_2$ 1470 cm$^{-1}$ (partially covered by the phosphine absorption) d. X rays. This method was the determinant for the structure resolution of the structure. As in the preceding example we observed a distorted trigonal bipyramidal structure around iridium. The ligands were: two ethylene molecules, two phosphorous atoms (of phosphines), one carbon atom of the phosphine ligand $CH_3$ and bound to iridium by a covalent bond, the Ir-C length being 2.14 A.

EXAMPLE 3

3.3 × 10$^{-3}$ mole of IrH$_5$ [P(C$_3$H$_7$)$_3$]$_2$ was dissolved in 25 cc of degassed and anhydrous benzene, in an autoclave. It was subjected to a propylene pressure of 9 atmospheres at 50° C for six hours. The solvent was removed under a propylene stream at 5° C and the red residue was again dissolved in a minimum amount of n-pentane. The crystallized compound was recrystallized from n-pentane.

Some red prismatic crystals were obtained, very remarkably affected by moisture and oxygen, but very long steady under an inert atmosphere. It was filtered under Ar and dried under vaccum.

All the aforesaid operations were carried out under an argon atmosphere. The characterization was performed through:

IR: $ν_a(C=C) = 1375$ cm$^{-1}$, $ν_s(C=C) = 1000$ cm$^{-1}$, $δ(C\diagup C) = 512$ cm$^{-1}$, $ν_{Ir-\triangleright} = 360$ and $395$ cm$^{-1}$ Mass spectrum: Parent ion (C$_3$H$_5$)Ir [P(C$_3$H$_7$)$_3$]$_2$ NMR: (values as δ from TMS, J as c/s, m = multiplet, d = doublet).

| H$_A$ | H$_B$ | H$_C$ | CH | CH$_3$ |
|---|---|---|---|---|
| 3.9 m | 3.2 d(broad) | 1.5 d | 2.3 oktet | 1.1 d |
| J$_{AB}$ = 6 | J$_{AB}$ = 6 | 1.4 d | J = 7 | 1.2 d |
| J$_{AC}$ = 11 | | J$_{AC}$ = 11 | | S = 7 |
| 1 H | 2 H | 2 H | 6 H | 36H |

EXAMPLE 4

3.5 × 10$^{-3}$ mole of Ir H$_5$ [P(tert-butyl)$_3$]$_2$ was treated as in example 2. The reaction solution was concentrated to a small volume under an ethylene stream and the residue was dissolved in degassed and anhydrous n-pentane under an argon atmosphere. Well shaped yellow crystals were slowly deposited from the solution at −20° C which exactly analyzed for Ir(ethylene)$_2$ 8 P(t-butyl)$_3$ P(t-butyl)$_2$ (C$_4$H$_8$)] the reaction yield was about 70%. The IR and NMR data agreed with the proposed structure both as to the bands and chemical shifts values and as to the integrative ratios.

EXAMPLE 5

3.1 × 10$^{-2}$ mole of H$_7$Re [(C$_6$H$_5$)$_3$P]$_2$ was dissolved in 50 cc of benzene free from air, in autoclave under an ethylene pressure of 7 atmospheres. It was kept at 60° C, under a magnetic stirring, for four hours, then it was concentrated under an ethylene stream up to 10 cc and was crystallized.

The crystals, filtered under argon, were dried. This characterization was carried out through IR, centesimal analysis, NMR, mass spectrometry. The inferred structure was the following one: Re(C$_2$H$_4$)$_2$ [P(C$_6$H$_5$)$_2$C$_6$H$_4$] [P(C$_6$H$_5$)$_3$]

EXAMPLE 6

1.0 × 10$^{-3}$ mole of Ir(C$_2$H$_4$)$_2$ (L-C)L, wherein L =P(C$_6$H$_5$)$_3$, dissolved in an 5 cc of toluene, was subjected in autoclave to a C$_3$H$_6$ pressure of 10 atmospheres at 45° C for 6 hours and then was suddenly cooled at −20° C.

A slow crystallization of the product occurred yielding orange-red prisms. They were filtered under argon and then dried under vacuum. All the operations were carried under an inert atmosphere.

The characterization was performed through spectrophotometry.

IR $ν_s(C=C) = 895$ cm$^{-1}$, $550(δ_C\diagup C)$ $ν_{Ir} \triangleright 360, 390$ cm$^{-1}$ NMR (values in δ, J in c/s, m = multiplet, d = doublet -continued

| $H_A$ | $H_B$ | $H_C$ |
| --- | --- | --- |
| 4.6 m | 3.1 d | 2.3 d (broad) |
| $J_{AC} = 12$ | $J_{AB} = 7$ | $J_{AC} = 12$ |
| $J_{AB} = 7$ | | |
| 1H | 2H | 2H |

EXAMPLE 7

0.1 mole of pentene-1 was put in autoclave together with $1.7 \cdot 10^{-3}$ mole of $Ir(C_2H_4)_2(L-C)L$, $L = P(C_3H_7)_3$, under one atmosphere of hydrogen. It was stirred for 14 hours and the liquid was distilled away. The distilled residue consisted of 70% pentane and some isomers of pentane. The solid residue, recrystallized from $CH_3OH$, was Ir $H_2L_2$.

EXAMPLE 8

$1.1 \cdot 10^{-3}$ mole of Ir(allyl) $[P(C_3H_7)_3]_2$ was dissolved in $3.5 \cdot 10^{-2}$ mole of 1-pentane in an autoclave under 5 atmospheres of ethylene. The solution was stirred by a magnetic stirrer at 60° C for 10 hours. It was cooled, the gas was recovered and analyzed by mass spectrometry. The solution was distilled and the distilled portion consisted of $1.4 \cdot 10^{-2}$ mole of isomer pentenes and $2.1 \cdot 10^{-2}$ mole 1.3 pentadiene (60% conversion with respect to 1-pentene fed to reaction).

The amount of ethane formed was equimolecular to the found: pentane was observed only in trace amounts.

EXAMPLE 9

$1.7 \cdot 10^{-3}$ mole of Ir $(C_2H_4)$ (L-C)L, $L = P(C_6H_5)_3$, was dissolved in a mixture formed by 2 cc of benzene and 2 cc ($1.75 \cdot 10^{-2}$ mole) of n-hexene in an autoclave under an argon atmosphere. It was stirred by a magnetic stirring at 130° C for 12 hours and then was cooled to room temperature. The liquid was distilled and analyzed.

Apart from the uncharged benzene, $8.0 \cdot 10^{-2}$ mole of dienes, $8.0 \cdot 10^{-2}$ mole of hexane (conversion as dienes equal to 47%) and isomer hexenes were obtained.

The gas chromatography analyses confirmed that the reaction selectivity was practically 100%.

EXAMPLE 10

$1.8 \cdot 10^{-3}$ mole of $Ir(C_2H_4)$ (L-C)L, $L = P(C_3H_7)_3$, was dissolved in 5 g ($6 \cdot 10^{-2}$ mole) of methylbutynole and 3.6 g ($6 \cdot 10^{-2}$ mole) of isopropyl alcohol under an inert atmosphere. Under a magnetic stirring, the solution was kept at 75° C for 20 hours. It was cooled and the mixture was distilled. The distilled portion, analyzed, gave the following composition:

methyl butenole = $1.7 \cdot 10^{-2}$ mole; acetone = $1.7 \cdot 10^{-2}$ mole at a quantitative yield with respect to the changed reagents.

Methyl butanole was present only in trace.

What we claim is:

1. A process for the preparation of a σ complex of a transition metal having catalytic properties and represented by the formula $$M(C_2H_4)_2(L-C)(L)$$

in which M is Ir or Re; L is an alkyl or aryl phosphine of formula $PR_3$ wherein R is an isopropyl, tert-butyl, or phenyl radical; and L-C is an alkyl or aryl phosphine ligand of formula $PR_2R^-$, in which R is as defined above $R^-$ represents the R radical less one hydrogen, said ligand being in coordination with the M atom, which comprises:

reacting a hydride complex of formula $$MH_xL_2$$

in which M and L are as defined above x is 5 if M is Ir or 7 if M is Re, with ethylene.

2. The process as claimed in claim 1 wherein R is an isopropyl radical and $R^-$ is a $C_3H_6$ radical.

3. The process as claimed in claim 1 wherein R is a tert-butyl radical and $R^-$ is a $C_4H_8$ radical.

4. The process as claimed in claim 1 wherein R is a phenyl radical and $R^-$ is a $C_6H_4$ radical.

5. The process as claimed in claim 1 wherein the reaction is carried out in the presence of an inert solvent selected from the aromatic and aliphatic hydrocarbons.

6. The process as claimed in claim 5 wherein the inert solvent is selected from the group of benzene, n-pentane, and toluene.

7. The process as claimed in claim 1 wherein the reaction is carried out in the absence of a solvent other than the ethylene acting as such.

8. The process as claimed in claim 1 wherein the reaction is carried out in the temperature range of 0° to 70° C.

9. The process as claimed in claim 1 wherein the reaction is carried out in the pressure range of one to 15 atmospheres.

10. A process for the preparation of a σ complex of a transition metal having catalytic properties and represented by the formula

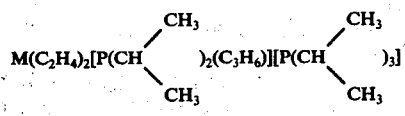

in which M is Ir or Re and

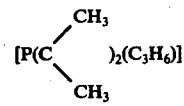

represents an alkyl phosphine ligand in coordination with the M atom, which comprises:

reacting a hydride complex of formula

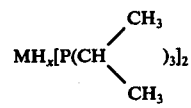

in which M is as defined above and x is 5 if M is Ir or 7 if M is Re, with ethylene.

11. A process for the preparation of a σ complex of a transition metal having catalytic properties and represented by the formula $$M(C_2H_4)_2[P(t\text{-}butyl)_2(C_4H_8)][P(t\text{-}butyl)_3]$$

in which M is Ir or Re and [P(t-butyl)$_2$(C$_4$H$_8$)] represents an alkyl phosphine ligand in coordination with the M atom, which comprises:

reacting a hydride complex of formula $$MH_x[P(t\text{-butyl})_3]_2$$

in which M is as defined above and x is 5 if M is Ir or 7 if M is Re, with ethylene.

12. A process for the preparation of a σ complex of a transition metal having catalytic properties and represented by the formula $$M(C_2H_4)_2[P(C_6H_5)_2(C_6H_4)] [P(C_6H_5)_3]$$

in which M is Ir or Re and [P(C$_6$H$_5$)$_2$(C$_6$H$_4$)] represents an aryl phosphine ligand in coordination with the M atom, which comprises:

reacting a hydride complex of formula $$MH_x[P(C_6H_5)_3]_2$$

in which M is as defined above and x is 5 if M is Ir or 7 if M is Re, with ethylene.

13. A process for the preparation of a π complex of a transition metal having catalytic properties and represented by the formula $$Ir(C_3H_5) (L')_2$$

in which L' is an alkyl or aryl phosphine of formula PR$_3$ wherein R is an isopropyl or phenyl radical; and the C$_3$H$_5$ radical is a ligand in coordination with the Ir atom, which comprises:

reacting a hydride complex of formula $$IrH_5L'_2$$

in which L' is as defined above, with propylene.

14. The process as claimed in claim 13 wherein R is an isopropyl radical.

15. The process as claimed in claim 13 wherein R is a phenyl radical.

16. The process as claimed in claim 13 wherein the reaction is carried out in the presence of an inert solvent selected from the aromatic and aliphatic hydrocarbons.

17. The process as claimed in claim 16 wherein the inert solvent is selected from the group of benzene, n-pentane, and toluene.

18. The process as claimed in claim 13 wherein the reaction is carried out in the absence of a solvent other than the propylene acting as such.

19. The process as claimed in claim 13 wherein the reaction is carried out in the temperature range of 0° to 70° C.

20. The process as claimed in claim 13 wherein the reaction is carried out in the pressure range of one to 15 atmospheres.

21. A process for the preparation of a π complex of a transition metal having catalytic properties and represented by the formula $$Ir(C_3H_5)[P(CH(CH_3)_2)_3]_2$$

in which the C$_3$H$_5$ radical is a ligand in coordination with the Ir atom, which comprises:

reacting a hydride complex of the formula $$IrH_5[P(CH(CH_3)_2)_3]_2$$

with propylene.

22. A process for the preparation of a π complex of a transition metal having catalytic properties and represented by the formula $$Ir(C_3H_5)[P(C_6H_5)_3]_2$$

in which the C$_3$H$_5$ radical is a ligand in coordination with the Ir atom, which comprises:

reacting a hydride complex of the formula $$IrH_5[P(C_6H_5)_3]_2$$

with propylene.

* * * * *

UNITED STATES PATENT AND TRADEMARK OFFICE
CERTIFICATE OF CORRECTION

PATENT NO. : 4,042,609
DATED : August 16, 1977
INVENTOR(S) : Emilio Perrotti et al.

It is certified that error appears in the above-identified patent and that said Letters Patent are hereby corrected as shown below:

Column 6, line 5, "above R-" should read --above and R- --;

line 12, "above x" should read --above and x--.

Signed and Sealed this

Seventh Day of March 1978

[SEAL]

Attest:

RUTH C. MASON
Attesting Officer

LUTRELLE F. PARKER
Acting Commissioner of Patents and Trademarks